US012778745B2

(12) United States Patent
Meijer

(10) Patent No.: US 12,778,745 B2
(45) Date of Patent: Nov. 3, 2026

(54) PLUNGER APPARATUS FOR A DELIVERY DEVICE

(71) Applicant: Alcon Inc., Fribourg (CH)

(72) Inventor: Robertus Meijer, Cambridge (GB)

(73) Assignee: Alcon Inc., Fribourg (CH)

( * ) Notice: Subject to any disclaimer, the term of this patent is extended or adjusted under 35 U.S.C. 154(b) by 757 days.

(21) Appl. No.: 18/017,463

(22) PCT Filed: Jun. 29, 2021

(86) PCT No.: PCT/GB2021/051649
§ 371 (c)(1),
(2) Date: Jan. 23, 2023

(87) PCT Pub. No.: WO2022/018396
PCT Pub. Date: Jan. 27, 2022

(65) Prior Publication Data

US 2023/0270539 A1 Aug. 31, 2023

(30) Foreign Application Priority Data

Jul. 23, 2020 (GB) ..................................... 2011447

(51) Int. Cl.
*A61F 2/16* (2006.01)

(52) U.S. Cl.
CPC ............ *A61F 2/1667* (2013.01); *A61F 2/167* (2013.01)

(58) Field of Classification Search
CPC .......... A61F 2/1667; A61F 2/167; A61C 5/62; A61M 5/34586; A61M 5/31581; A61M 5/31528; A61B 5/150236
See application file for complete search history.

(56) References Cited

U.S. PATENT DOCUMENTS 5,129,825 A 7/1992 Discko
2001/0007075 A1* 7/2001 Hjertman .............. A61F 2/1667 606/107
2005/0282117 A1 12/2005 Aravena et al.
(Continued)

FOREIGN PATENT DOCUMENTS

JP 11-510711 9/1999
JP 2010-521275 6/2010
(Continued)

OTHER PUBLICATIONS

International Search Report and the Written Opinion Dated Oct. 4, 2021 From the International Searching Authority Re. Application No. PCT/GB2021/051649. (10 Pages).
(Continued)

*Primary Examiner* — Anh T Dang
(74) *Attorney, Agent, or Firm* — Sanders IP Law

(57) ABSTRACT

Plunger apparatus comprising a housing, a plunger, a source of stored mechanical energy, a rotatable element and an actuator. Rotation of the rotatable element provides a controlled release of the plunger for the movement of the plunger, under force provided by the source of stored mechanical energy. The actuator allows operation, by an operator, of the plunger apparatus to induce rotation of the rotatable element relative to the housing to provide a controlled release of the plunger for axial movement of the plunger under the force provided by the source of stored mechanical energy.

24 Claims, 5 Drawing Sheets

(56) References Cited

U.S. PATENT DOCUMENTS

| | | | | |
|---|---|---|---|---|
| 2014/0257315 | A1* | 9/2014 | Wu | A61F 2/1672 606/107 |
| 2015/0066044 | A1* | 3/2015 | Woods | A61F 2/1678 606/107 |
| 2016/0220327 | A1 | 8/2016 | Tapocik | |
| 2017/0172727 | A1 | 6/2017 | Kanner | |
| 2019/0117897 | A1 | 4/2019 | Avery et al. | |
| 2019/0274825 | A1 | 9/2019 | Kanner | |
| 2020/0197161 | A1 | 6/2020 | Wu | |

FOREIGN PATENT DOCUMENTS

| | | |
|---|---|---|
| JP | 2016-163721 A | 9/2016 |
| WO | WO 96/37152 | 11/1996 |
| WO | WO 2008/116766 | 10/2008 |
| WO | WO 2013/029999 | 3/2013 |
| WO | WO 2013/184727 | 12/2013 |
| WO | WO 2014/089250 | 6/2014 |
| WO | WO 2014/1654345 | 10/2014 |
| WO | WO 2016/141308 | 9/2016 |
| WO | WO 2017/214392 | 12/2017 |
| WO | WO 2019/053100 | 3/2019 |
| WO | WO 2019/236355 | 12/2019 |

OTHER PUBLICATIONS

Patents Act 1977: Search Report Under Section 17(5) Dated Jan. 22, 2021 From the Intellectual Property Office of the United Kingdom of Great Britain Re. Application No. GB2011447.6. (4 Pages).

* cited by examiner

PLUNGER APPARATUS FOR A DELIVERY DEVICE

RELATED APPLICATIONS

This application is a National Phase of PCT Patent Application No. PCT/GB2021/051649 having International filing date of Jun. 29, 2021, which claims the benefit of priority of United Kingdom Patent Application No. 2011447.6 filed on Jul. 23, 2020. The contents of the above applications are all incorporated by reference as if fully set forth herein in their entirety.

FIELD AND BACKGROUND OF THE INVENTION

The present invention relates to plunger apparatus, for a delivery device for deploying a substance or object, and to associated methods. The present invention has particular, but not exclusive, relevance to plunger apparatus for a device for implantation of an intraocular lens (IOL) into an eye of a subject and corresponding methods for manufacturing and using such apparatus.

There are many medical and non-medical procedures in which a medical practitioner or other operator is required to dispense a viscous substance, or to deploy a small object (often held in a viscous medium), in a precise and controlled manner. Such procedures typically require a highly skilled operator to apply a relatively high force, often on a routine basis, whilst maintaining a high level of accuracy.

One such application is the implantation of an intraocular lens (IOL) into the eye of a patient as part of a procedure for treating medical conditions such as cataracts or myopia.

To support such procedures, IOL injectors or insertion devices have developed that allow a surgeon to insert an IOL, into the eye of a patient, through an incision that is considerably narrower than the width of the lens. These devices typically fold the lens into a smaller size by advancing it, with a plunger, through a narrow nozzle. For clinical reasons a viscous agent, known as a viscoelastic or 'ophthalmic viscosurgical device' ('OVD'), is added as the lens is offered up to the nozzle.

The friction between the lens and the nozzle of an IOL injector can be high and, depending on the size and type of the lens, the delivery plunger may therefore have to be driven with a correspondingly high force by the responsible practitioner. The delivery must be executed in a very controlled manner to avoid a quick release of stored energy at the moment the lens exits the nozzle and enters the eye.

Existing devices typically come in the form of syringe-like, manually driven, delivery devices. However these can be difficult for an operator to control, particularly when the IOL exits the injector, because of the sharp drop in the force necessary for delivery, from the relatively high level required to push the lens through the nozzle, to almost zero immediately after the lens has left the nozzle. As the force drops suddenly, there is a risk that the operator may lose control of the device and, as a result, that the nozzle, which rests in a minute incision in the eye, causes an ocular injury.

Whilst the risk associated with the step-change in application force may be ameliorated in manually operated screw based IOL delivery devices, these devices tend to deliver lenses relatively slowly. Moreover, the rotational movements made by the operator to operate a screw based or similar device can cause undesirable movement of the nozzle with an associated risk that eye tissue can be torn adjacent the incision.

In general, manually operated screw based devices also require two hands for operation. However, there is a preference amongst surgeons to have one hand free to help steady the patient's eye during lens implantation and to guide the emerging lens into location. Electrically driven, hydraulically driven, compressed gas driven and spring driven types of delivery mechanisms have been contemplated, and introduced into the marketplace. Whilst these have the benefit that they can free a surgeon's hand to assist in the insertion procedure, existing devices tend to be heavy, poorly balanced, mechanically complex and expensive.

It will be appreciated that analogous issues can arise with any similar delivery device for other applications in which an operator is required to dispense a viscous substance, or to deploy a device held in a viscous medium, in a precise and controlled manner. Even where the force or precision required is not particularly great, there is a risk of repetitive strain injury in any similar procedure where an operator is required to use such a delivery device routinely.

SUMMARY OF THE INVENTION

The invention aims to provide an improved plunger apparatus and an associated method, for example plunger apparatus for a delivery device that overcomes or at least partially ameliorates one or more of the above issues, and one or more associated methods for manufacturing or using such plunger apparatus.

Aspects of the invention are set out in the appended independent claims. Other optional features are recited in the dependent claims.

According to one example there is provided plunger apparatus for a delivery device, the plunger apparatus comprising: a housing; a plunger configured for movement in an axial direction relative to the housing for expelling at least one object and/or material from a nozzle of the delivery device; a source of stored mechanical energy for providing a force for driving the movement of the plunger in the axial direction relative to the housing; a rotatable element held by the housing and configured for rotation relative to the housing, whereby rotation of the rotatable element provides a controlled release of the plunger for the movement of the plunger, in the axial direction relative to the housing, under the force provided by the source of stored mechanical energy; and an actuator for operation by an operator of the plunger apparatus to induce rotation of the rotatable element relative to the housing to provide the controlled release of the plunger for the axial movement of the plunger under the force provided by the source of stored mechanical energy.

The rotation of the rotatable element may, for example, be about an axis of rotation that is parallel to the axial direction. Where the rotation of the rotatable element is through a given cumulative rotational displacement, the plunger apparatus may be configured for movement of the plunger, in the axial direction relative to the housing, for a longitudinal displacement that is dependent on the cumulative rotational displacement.

The plunger and the housing may be mutually configured for axial movement relative to one another in which rotation of the plunger, relative to the housing as the plunger moves in the axial direction, is inhibited. The plunger and the rotatable element may each have a respective threaded surface. Where the plunger and the rotatable element each have a respective threaded surface, the threaded surfaces of the plunger and the rotatable element may, optionally, be configured for mutual engagement whereby the rotatable element may be configured for rotation relative to the plunger as the rotatable element rotates relative to the housing to provide the controlled release of the plunger.

Where the plunger and the rotatable element each have a respective threaded surface, the threaded surfaces of the plunger and the rotatable element may be configured such that the rotatable element is back-drivable with respect to the plunger. The threaded surfaces of the plunger and the rotatable element may be configured for inhibiting the axial movement of the plunger, relative to the housing, when the rotatable element is not being rotated.

The rotatable element and plunger may be mutually configured for axial movement relative to one another in which rotation of the rotatable element, relative to the plunger, as the plunger moves in the axial direction, is inhibited.

The plunger and the housing may each have a respective threaded surface. When the plunger and the housing each have a respective threaded surface, the threaded surfaces of the plunger and the housing may optionally be configured for mutual engagement whereby the plunger is configured for rotation relative to the housing, as the rotatable element rotates relative to the housing, to provide the controlled release of the plunger.

The rotatable element and housing may be mutually configured for rotational movement relative to one another in which axial movement of the rotatable element, relative to the housing, is inhibited.

The source of stored mechanical energy may comprise a spring that is arranged for storing elastic potential energy, prior to actuation of the plunger apparatus, for providing the force for driving the movement of the plunger. The spring may be arranged to be in a compressed state for storing the elastic potential energy prior to actuation of the plunger apparatus for providing the force for driving the movement of the plunger. Alternatively, the spring may be arranged to be in a tensioned state for storing the elastic potential energy prior to actuation of the plunger apparatus for providing the force for driving the movement of the plunger.

The source of stored mechanical energy may comprise a pneumatic actuator for providing a pneumatic force as the force for driving the movement of the plunger.

The actuator may be configured for axial movement, by the operator, relative to the housing whereby the axial movement of the actuator may induce the rotation of the rotatable element relative to the housing to provide the controlled release of the plunger. The actuator and the housing may be mutually configured for axial movement relative to one another in which rotation of the actuator, relative to the housing as the actuator is moved in the axial direction, may be inhibited.

The actuator and the rotatable element may each have a respective threaded surface. Where the actuator and the rotatable element each have a respective threaded surface, the threaded surfaces of the actuator and the rotatable element may, optionally, be configured for mutual engagement whereby the rotatable element is configured for rotation relative to the actuator, as the actuator is moved in the axial direction, whereby to provide the controlled release of the plunger. The threaded surfaces of the actuator and the rotatable element may be configured such that the rotatable element is back-drivable with respect to the actuator.

The rotatable element and actuator may be mutually configured for axial movement relative to one another in which rotation of the rotatable element, relative to the actuator, as the actuator moves in the axial direction, may be inhibited.

The actuator and the housing may each have a respective threaded surface. Where the actuator and the housing each have a respective threaded surface, the threaded surfaces of the actuator and the housing may optionally be configured for mutual engagement whereby the actuator is configured for rotation relative to the housing, to rotate the rotatable element relative to the housing whereby to provide the controlled release of the plunger.

The actuator may be provided with an electro-mechanical mechanism for driving rotation of the rotatable element relative to the housing and, optionally, with a switch for operation of the electro-mechanical mechanism, by an operator, to control operation of the rotatable element whereby to provide the controlled release of the plunger.

The plunger apparatus may also comprise at least one further source of mechanical energy for providing a force for driving the rotation of the rotatable element. For example, the at least one further source of mechanical energy may comprise a spring, such as a torsion spring or the like, and/or may comprise a electrically powered source of mechanical energy.

The plunger apparatus may also comprise at least one element for providing a preconfigured resistance between the actuator and the housing for resisting axial movement of the actuator relative to the housing whereby the actuator may be moveable by an operator, for example by applying a substantially uniform force that is sufficient for overcoming the preconfigured resistance.

The housing, plunger, rotatable element and the actuator may be mutually configured for operation of the actuator by an operator applying a substantially uniform force for moving the actuator in the axial direction, whereby to rotate the rotatable element relative to the housing to provide the controlled release of the plunger; from a first position relative to the housing in which the plunger apparatus is primed for use; to a second position relative to the housing in which the plunger apparatus is configured to expel the at least one object and/or material from the nozzle of the delivery device in operation.

According to one example there is provided a delivery device for expelling at least one object and/or material, the delivery device comprising a nozzle for expelling the at least one object and/or material and a plunger apparatus as claimed in any preceding claim.

The delivery device may be configured for expelling an intraocular lens into the eye of a patient.

According to one example there is provided a method for expelling at least one object and/or material, the method comprising: providing the above mentioned delivery device, the delivery device containing the at least one object and/or material to be expelled; and operating the actuator of the plunger apparatus of the delivery device apparatus to induce rotation of the rotatable element relative to the housing to provide the controlled release of the plunger for the axial movement of the plunger under the force provided by the source of stored mechanical energy, whereby to expel the at least one object and/or material.

According to one example there is provided a method of manufacturing the above mentioned plunger apparatus, the method comprising: providing the housing, the plunger, the source of stored mechanical energy, the rotatable element, and the actuator of the plunger apparatus; and assembling the housing, the plunger, the source of stored mechanical energy, the rotatable element, and the actuator to form the plunger apparatus.

BRIEF DESCRIPTION OF THE SEVERAL VIEWS OF THE DRAWINGS

Embodiments of the invention will now be described, by way of example, with reference to the accompanying drawings in which:

FIG. 1(*b*) is an illustration showing, schematically, a three-dimensional view of the exemplary plunger apparatus of FIG. 1(*a*) when employed as part of a delivery device for an intraocular lens (IOL);

FIG. 2(*b*) is an illustration showing, schematically, a three-dimensional view of part of the exemplary plunger apparatus of FIG. 1(*a*);

FIG. 3(*b*) is an illustration showing, schematically, another three-dimensional sectional view of the exemplary plunger apparatus of FIG. 1(*a*);

DESCRIPTION OF SPECIFIC EMBODIMENTS OF THE INVENTION

Figure 1B:
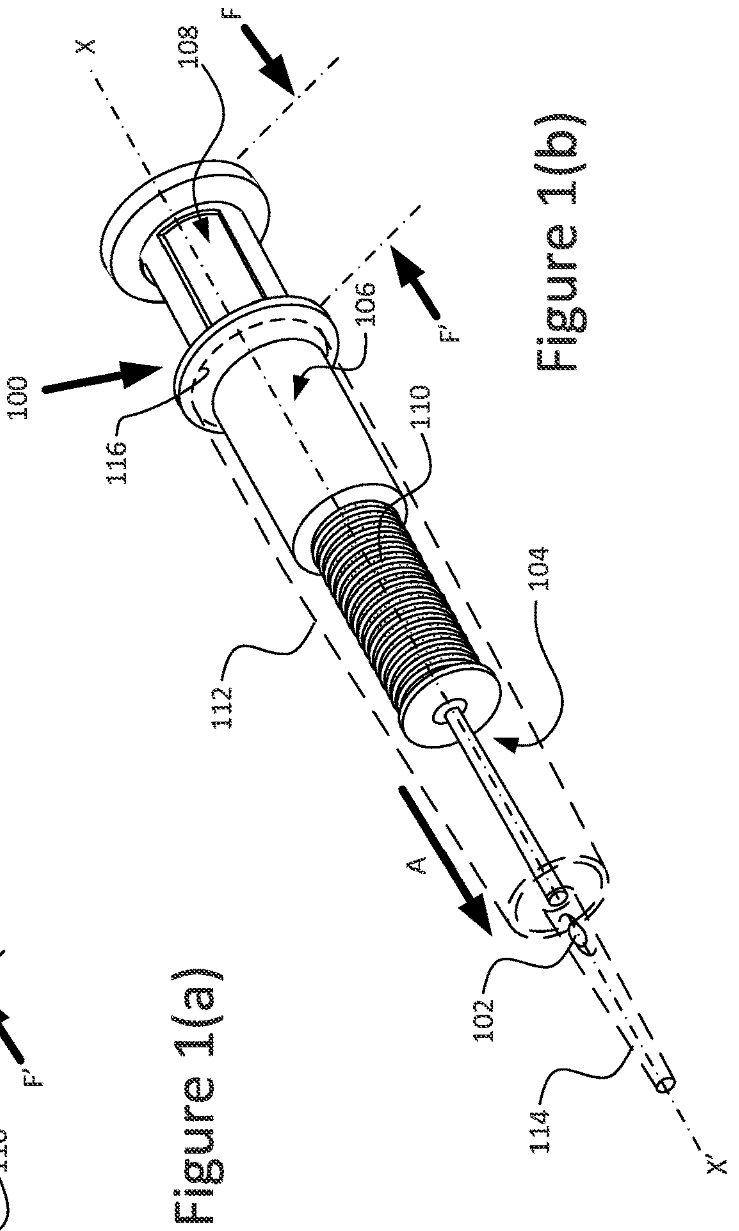
FIG. 1(*a*) is an illustration showing, schematically, a three-dimensional view of an exemplary plunger apparatus for a delivery device.
Figure 1A:
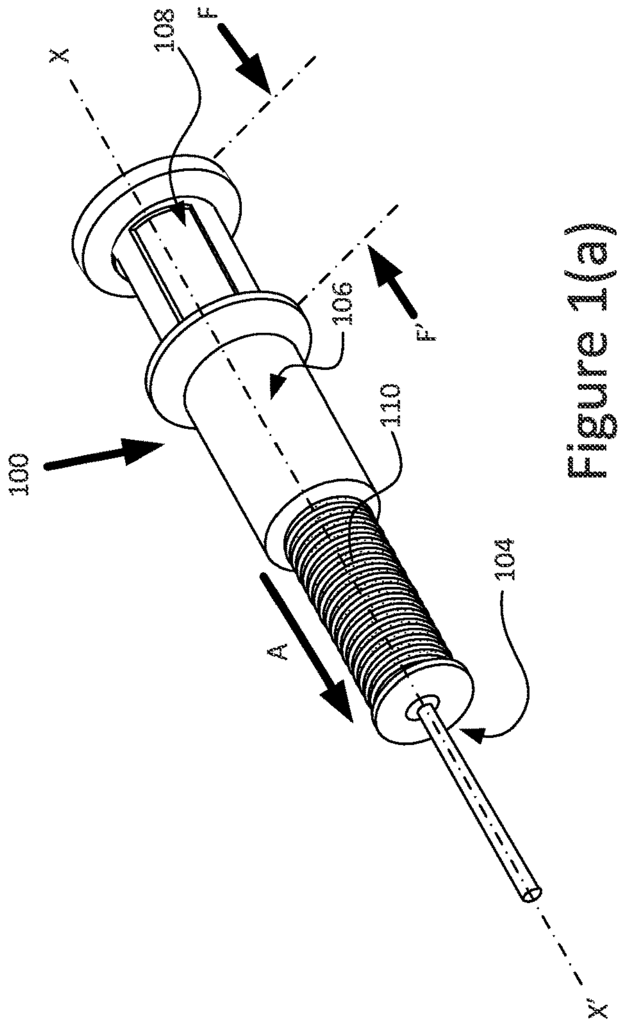

FIGS. 1(*a*) and 1(*b*) show, generally at 100, plunger apparatus for a delivery device. FIG. 1(*a*) is an illustration showing, schematically, a three-dimensional view of an exemplary plunger apparatus for a delivery device. FIG. 1(*b*) is an illustration showing, schematically, a three-dimensional view of the plunger apparatus 100 of FIG. 1(*a*) employed as part of a delivery device for deployment an intraocular lens (IOL) 102.

As seen in FIG. 1(*a*), the plunger apparatus 100 resembles a medical syringe or the like and comprises a plunger 104, a housing 106, an actuator 108 and a spring 110 that are arranged coaxially relative to their longitudinal axes (i.e. relative to axis X-X' in FIGS. 1(*a*) and 1(*b*)). The housing 106 is configured to slidably receive part of the plunger 104 into one end of the housing 106 and part of the actuator 108 into the other end of the housing 106. The spring 110 comprises a compression spring that, when the plunger apparatus 100 is fully assembled and ready for use, is in a pre-compressed state. The spring 110 is arranged to provide a driving force for driving the plunger 104, in the direction of arrow A, away from the actuator 108 and housing 106.

As seen in FIG. 1(*b*) the IOL delivery device comprises an elongated sheath like covering 112 of generally circular cross-section. The covering 112 forms an internal chamber in which the IOL 102 (along with any viscoelastic agent/ophthalmic viscosurgical device (OVD)) is located for deployment. The covering 112 has a nozzle 114, provided longitudinally at one end of the internal chamber (coaxially with axis X-X'), through which the IOL 102 located in the chamber may be driven by the plunger 104 during operation. An opening 116, is provided longitudinally at the end of the internal chamber opposite the nozzle 114, for receiving the plunger apparatus 100 for assembly to form the IOL delivery device. It will be appreciated that the illustration of the IOL delivery device is provided for the purposes of illustrating how the plunger apparatus 100 may be used and is simplified for reasons of clarity.

The plunger apparatus 100 is arranged such that, in operation, a user of the plunger apparatus 100 can operate the device by applying a relatively low and generally constant force between the actuator 108 and the housing 106 (as indicated by arrows F-F') to slide the actuator in the direction of arrow A. For example, the device can be operated using one hand by the user pressing the actuator 108 with a thumb whilst retaining the housing 106 in position between two fingers in the manner of a syringe.

Beneficially, the internal features of the plunger apparatus 100 are configured to decouple the force required to move the plunger 104 (the 'plunger force') from the force that has to be applied to the actuator 108 (the 'actuation force'), relative to the housing 106, to operate the device. Specifically, as will be described in more detail later, the internal features of the plunger apparatus 100 are configured such that, when a relatively low and constant force is applied to the actuator, the movement of the actuator as it slides into the housing 106 triggers corresponding movement of the plunger 104. The features of the plunger apparatus 100 are beneficially configured such that the plunger 104 is driven, in the direction A, entirely (or at least predominantly) by the spring force exerted by the pre-compressed spring 110.

The internal features of the plunger apparatus 100 are also configured such that when the plunger apparatus 100 is assembled, and no force is applied to the actuator, the plunger 104 is maintained in its position and the spring force cannot drive the plunger 104 in the direction of arrow A. The movement of actuator 106 by the operator therefore controls the displacement of the plunger 104 and the speed of delivery.

Thus, during operation by a user such as a surgeon, when implemented as part of an IOL delivery device, the plunger 104 presses the IOL through the tightest cross-section of the nozzle 114 into the anterior chamber of the eye. The relatively high force required to achieve this (potentially up to 50N depending on lens selection and choice of viscoelastic agent) is provided by the spring 110. When the insertion force drops dramatically, once most of the lens has passed through the narrowest section of the nozzle 114, the fine control required to prevent trauma to the eye is provided by fine adjustment of the actuator 108.

It can be seen, therefore, that the exemplary plunger apparatus introduced above has application in an IOL delivery device (or similar device) for the relatively effortless insertion of an IOL (or for the delivery of other objects or viscous materials), in a one-handed manner. The exemplary delivery device represents an improvement with respect to many existing one-handed devices by lowering the force that a surgeon needs to apply to force the lens through the nozzle and improving control when the lens exits the nozzle. The force required to push the IOL through the nozzle 114 would otherwise be uncomfortably high for it to be delivered single-handedly.

Plunger Apparatus

Figures 2A, 2B:
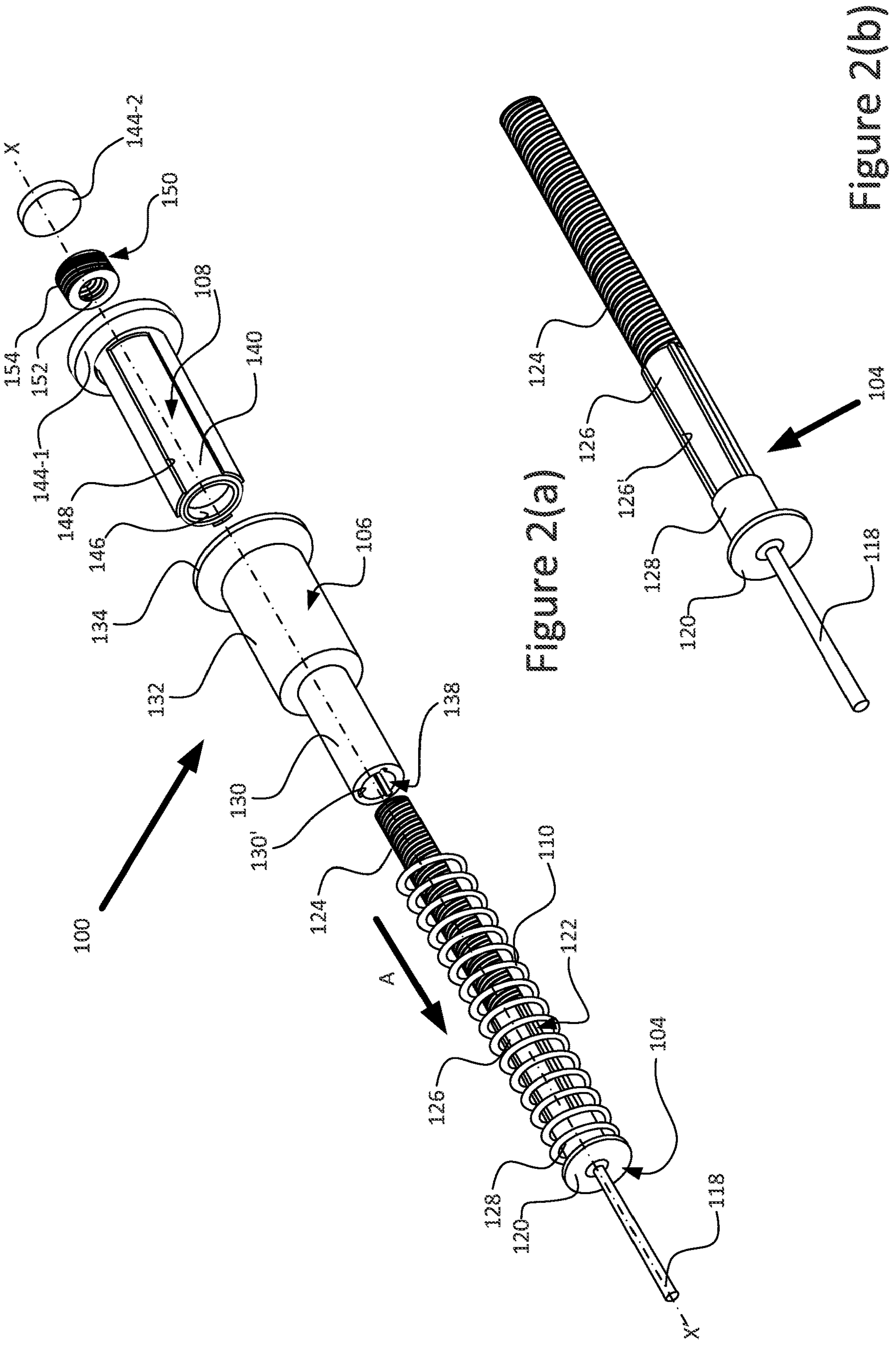
FIG. 2(*a*) is an illustration showing, schematically, a three-dimensional exploded view of the exemplary plunger apparatus of FIG. 1(*a*)

The plunger apparatus 100 will now be described in more detail, by way of example only, with reference to FIGS. 2(*a*) and 2(*b*), and FIGS. 3(*a*) and 3(*b*). FIG. 2(*a*) is an illustration showing, schematically, a three-dimensional exploded view of the plunger apparatus 100 of FIG. 1(*a*). FIG. 2(*b*) is an illustration showing, schematically, a three-dimensional view of the plunger 104 of the plunger apparatus 100. FIG.

3(*a*) is an illustration showing, schematically, a three-dimensional sectional view of the plunger 104 and the housing 106 of the exemplary plunger apparatus 100 of FIG. 1(*a*) in a partially assembled state. FIG. 3(*b*) is an illustration showing, schematically, a three-dimensional sectional view of the plunger 104, the housing 106, and the actuator 108 of the exemplary plunger apparatus 100 of FIG. 1(*a*) in an assembled state.

As seen in FIGS. 2(*a*) to 3(*b*), the plunger 104 comprises a plunger tip 118 for pushing the IOL 102 from the nozzle 114 of the IOL delivery chamber, a generally disc shaped spring retainer 120 for retaining the spring 110, and a generally cylindrical plunger body 122. The plunger tip 118, spring retainer 120, and plunger body 122 are arranged coaxially relative to one another along a common central axis (axis X-X'). The plunger body 122 extends from the spring retainer 120 in one direction along the central axis X-X' and the plunger tip 118 extends in the opposite direction.

The plunger body 122 comprises a threaded portion 124, an interlocking portion 126, and a plunger stop 128 arranged along the central axis X-X'. The threaded portion 124 is located at an end of the plunger body 122 that is furthest from the plunger tip 118; the plunger stop 128 is located at an end of the plunger body 122 that is closest to the plunger tip 118; and the interlocking portion 126 is located between plunger stop 128 and the threaded portion 124.

The housing 106 comprises a first hollow, elongate, generally cylindrical casing portion 130 and a second hollow, elongate, generally cylindrical casing portion 132. The first casing portion 130 has a smaller diameter than, and is coaxially aligned with, the second casing portion 132. The first casing portion 130 extends away from the second casing portion 132 towards the plunger tip end of the plunger apparatus 100 when assembled.

A generally annular shaped flange 134 is provided at an end of the second casing portion 130 that is furthest from the plunger tip 118 when the plunger apparatus 100 has been assembled. The flange 134 has a larger diameter than, and is coaxially aligned with, the second casing portion 132. The flange 134 thus allows a user to engage a pair of fingers against a plunger side surface of the flange, during operation, to retain the housing 106 in position while applying pressure to the actuator 108 in the manner of a syringe or the like.

Figures 3A, 3B:
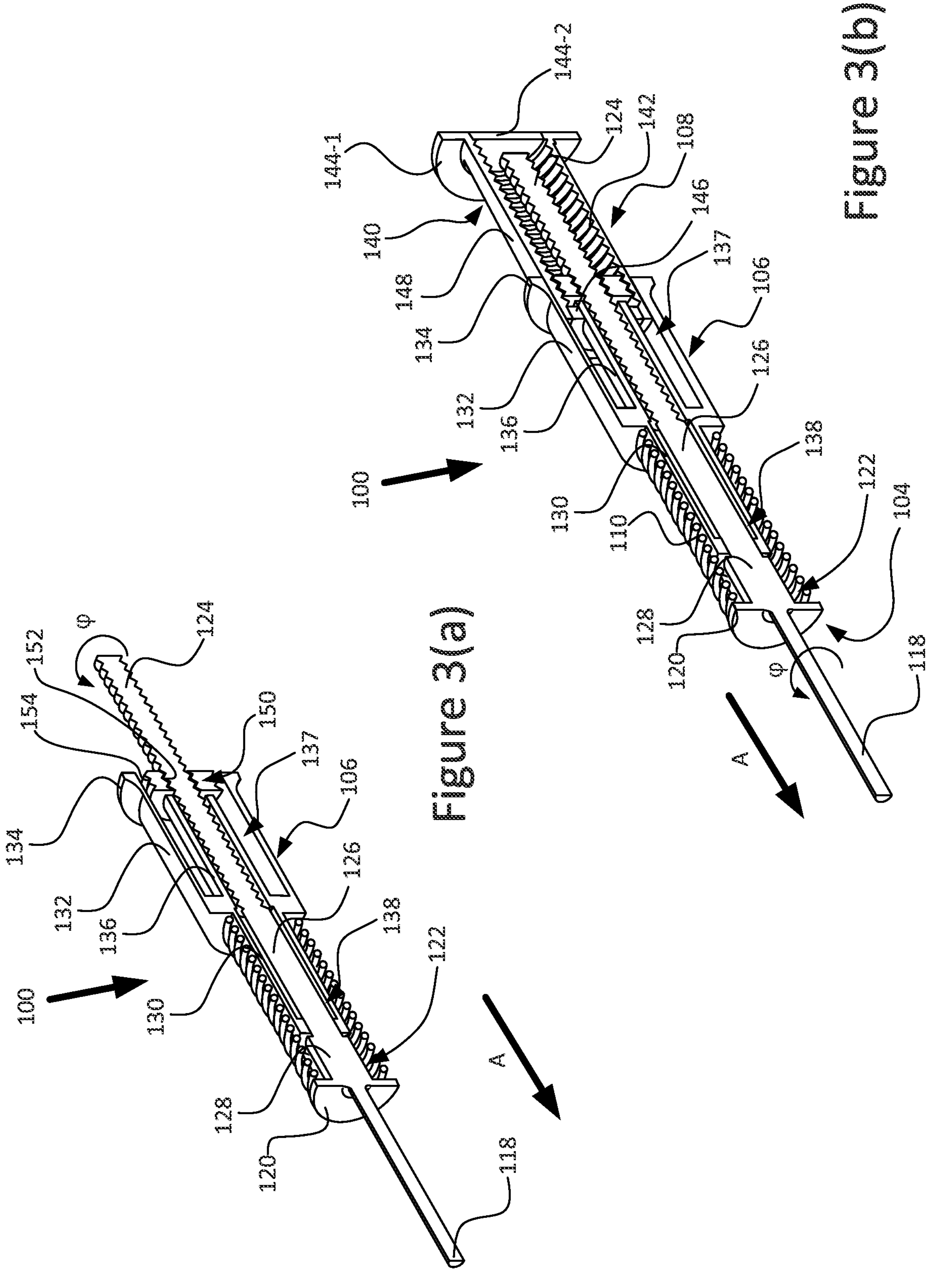
FIG. 3(*a*) is an illustration showing, schematically, a three-dimensional sectional view of part of the exemplary plunger apparatus of FIG. 1(*a*)

As best seen in FIGS. 3(*a*) and 3(*b*), the housing 106 is also provided with a hollow, elongate, generally cylindrical internal portion 136 that extends in an opposite direction to the first casing portion 130, into the second casing portion 132. The internal portion 136 has a smaller diameter than, and is coaxially aligned with, an inner chamber formed by the second casing portion 132. Thus, the internal portion 136 and second casing portions 130 together define a chamber 137 of annular cross-section within second casing portion 132.

The internal portion 136 and first casing portion 130 each define a respective, generally cylindrical, interior chamber that is open at both ends. These internal chambers, being coaxially aligned with one another, form a substantially continuous central channel 138 that is open at both ends. The internal portion 136 and first casing portion 130 of the housing 106, and the threaded portion 124 and interlocking portion 126 of the plunger body 122, have shape and dimensions that are mutually configured to allow the threaded portion 124 and interlocking portion 126 to be slidably received into and through the central channel 138 of the housing 106, when the plunger apparatus 100 is assembled.

The first casing portion 130 and the plunger stop 128 of the plunger body 122 are mutually configured such that when the plunger body 122 is slidably received into the central channel 138, during assembly, the plunger stop 128 will, ultimately, engage against the end of the first casing portion 130 that is closest to the plunger tip 118, and inhibit further movement of the plunger body 122 into the central channel 138.

The interlocking portion 126 of the plunger body 122 is of approximately the same length as the first casing portion 130 and, as seen in FIG. 2(*b*), comprises a plurality of keying features 126'. These keying features 126' are configured for engaging with mutually compatible keying features 130', provided in the first casing portion 130, to inhibit rotation of the plunger 104 when the plunger body 122 has been received in the central channel 138. In this example, the keying features 126' of the interlocking portion 126 comprise a plurality of splines that extend the length of the interlocking portion 126. The keying features 130' of the first casing portion 130 comprise a plurality of grooves that extend along the central channel 138, for the length of the first casing portion 130, and are configured to engage with the splines 126'. It will be appreciated, however, that any suitable mechanism may be used to inhibit rotation of the plunger 104.

The threaded portion 124 of the plunger body 122 has a length that is greater than that of the length of the second casing portion 132 of the housing 106 such that when the plunger body 122 has been fully received into the central channel 138, with the plunger stop 128 abutting the first casing portion 130, the threaded portion extends through and beyond the end of the second casing portion 132 that is furthest from the plunger tip 118.

The actuator 108 comprises an elongate, generally cylindrical, hollow actuator body 140 having one or more spiral grooves provided on its inside face to form an internal threaded surface 142, and a generally circular opening respectively at each end. An actuator button 144 is provided at an end of the actuator 108 that is furthest from the plunger tip 118 when the plunger apparatus 100 is assembled. The actuator button 144 comprises a generally annular portion 144-1, that has a larger diameter than and is coaxially aligned with the actuator body 140, and a cap 144-2. The annular portion 144-1 and the actuator body 140 are mutually configured to define a recess into which the cap 144-2 can be removably received to close off the actuator 108 at the end that is furthest from the plunger tip 118.

A friction element 146 is provided around the inner surface of the opening at the end of the actuator 108 that is furthest from the plunger tip 118. As seen in FIG. 3(*b*), the friction element 146 is configured to mutually engage with the cylindrical internal portion 136 of the housing 106, when the plunger apparatus 100 is assembled, to provide a constant resistive force as the actuator 108 is pushed into the housing 106, along axis X-X', in the direction of arrow A.

The friction element 146 may comprise any suitable mechanism for providing the required amount of resistance to movement of the actuator 108. In this example, the friction element comprises a ring of appropriate material (e.g. rubber or the like) that is configured to fit around the internal portion 136 of the housing 106, when the plunger apparatus 100 is assembled, as seen in FIG. 3(*b*). It can be seen, therefore, that the friction element is analogous to the rubber bung, or the like, that provides friction during operation of a disposable syringe. It will be appreciated, however, that a similar friction element may alternatively or additionally be provided around the outer surface of the actuator body 140 for engagement against an internal surface of the second casing portion 132 of the housing 106. Moreover, a more sophisticated arrangement may be used in which the friction element 146 and/or related feature(s) of the housing 106 are specially configured to reduce the difference between static and kinetic friction.

The second casing portion 132 of the housing 106, and the actuator body 140, are mutually configured for slidable reception of the actuator body 140, into the housing 106, from the end of second casing portion 132 that is furthest from the plunger tip 118, during operation. The second casing and internal portions 132, 136 of the housing 106, the actuator body 140, and the friction element 146 are mutually configured such that, as the actuator body 140 slides into the housing 106 and the end of the actuator 108 closest to the plunger tip 118 enters the chamber 137 annular cross-section, the friction element 146 engages around and against an outer surface of the internal portion 136 to provide the constant resistive force against the movement of the actuator 108.

The actuator body 140 also comprises a plurality of keying features 148 for engaging with corresponding keying features provided in the second casing portion 132 to inhibit rotation of the actuator 108, when the actuator body 140 has been slideably received in the housing 106. In this example, the keying features 148 of the actuator body 140 comprise a plurality of splines that extend substantially the length actuator body 140.

The keying features of the second casing portion 132 comprise a plurality of grooves that extend substantially the length of the second casing portion 132 and are configured to engage with the splines 148 of the actuator body. It will be appreciated, however, that any suitable mechanism may be used to inhibit rotation of the actuator 108.

The spring 110 is provided around, and coaxially aligned with, the plunger body 122 and first casing portion 130. The plunger body 122 and casing portions 130, 132 of the housing are configured such that, when the plunger apparatus 100 is fully assembled and ready for use, the spring is in a pre-compressed state and is retained between the spring retainer 120 of the plunger apparatus 100, and the end of the larger diameter second casing portion 132. Thus, the spring exerts a spring force on the plunger 104, in the direction of arrow A, away from the actuator 108 and housing 106.

As seen in FIGS. 2(*a*) to 3(*b*), the plunger apparatus 100 is also provided with a rotatable element that, in this example, is in the form of a nut 150. The nut 150 has an internal threaded surface 152 and an external threaded surface 154.

The internal threaded surface 152 of the nut 150 and threaded portion 124 of the plunger body 122 are mutually configured for engaging with one another to allow the nut 150 to be threaded onto the threaded portion 124, and to move linearly relative to the threaded portion 124, as the nut 150 rotates about the central axis X-X'. In this example, the thread of the internal threaded surface 152 of the nut 150 and the thread of the threaded portion 124 are of relatively high pitch and are mutually configured so that if the nut 150 is rotated in a direction, φ, the displacement of the nut 150 relative to the plunger tip 118 increases (and vice versa). In this example, the thread of the threaded portion 124 beneficially has a plurality of thread starts although it will be appreciated that this need not be the case.

By way of illustration, in this example of a back-drivable plunger, a typical range for the pitch is between once and twice the pitch diameter of the plunger thread although it will be appreciated that material selection is influential on the optimum pitch and so values outside this range may be suitable depending on the material used.

The external threaded surface 154 of the nut 150 and the internal threaded surface 142 of the actuator body 140 are mutually configured for engaging with one another to allow the nut 150 to be threaded into the actuator body 140, and to move linearly relative to the actuator body 140, as the nut 150 rotates about the central axis X-X'. In this example, the thread of the external threaded surface 154 of the nut 50 and the thread of the internal threaded surface 142 of the actuator body 140 are of relatively high pitch and are mutually configured so that if the nut 150 is rotated in a direction, φ, the displacement of the nut 150 relative to the actuator button 144 decreases (and vice versa). In this example, the thread of the internal threaded surface 142 beneficially has a plurality of thread starts although it will be appreciated that this need not be the case.

As seen in FIG. 3(*b*), when the plunger apparatus 100 is fully assembled, the nut 150 is located both in threaded engagement on the threaded portion 124 of the plunger body 122, and in threaded engagement with the internal surface 142 of the actuator body 140. The nut 150 is located within the actuator body 140, between the friction element 146 and the actuator button 144, abutting the end of the internal portion 136 of the housing 106. Thus, linear movement of the nut 150 towards the plunger tip 118, in the direction of arrow A, is inhibited. This mechanism thus allows the displacement of the plunger tip 118 to be controlled by the rotation of the nut 150.

In this example, the threads at the interface between the threaded portion 124 and the nut 150 are configured so that the nut 150 is back-driveable with respect to the plunger body 122. Thus, as an operator exerts a force on the actuator button 144 to slide the actuator body 140 into the housing 106, movement of the actuator 108 is not inhibited by the nut 150. Instead, the nut 150 begins to rotate within the actuator body 140, and around the treaded portion 124 of the plunger body 122, without axial movement of the nut 150 because axial movement is inhibited by the internal portion 136 of the housing 106. The plunger 104 thus begins to move axially, in the direction of arrow A, under the force exerted by the spring 110 against the spring retainer 120, without rotating because rotation of the plunger 104 is inhibited by the keying features 126' of the interlocking portion 126.

It can be seen that the rotation of the nut 150 through a given cumulative rotational displacement thus provides a release of the plunger in the direction of arrow A, under the force provided by the spring 110, for a cumulative axial displacement that is commensurate with that rotational displacement. This dependency between rotational and linear displacement allows for significantly improved control over clutch mechanisms, and the like, which operate to hold the plunger against the spring force, until the clutch or similar mechanism is operated and the spring is released more suddenly and in a less controlled manner. The dependency between the rotational and linear displacement will typically be a proportional relationship in which a relatively large rotational displacement of the nut 150 provides for a relatively small axial movement of the plunger in the longitudinal direction of arrow A.

The force an operator, such as a surgeon, exerts on the actuator 108 is therefore effectively a constant force. This substantially constant force is equal to the force required to overcome the resistive force provided by the friction element 146, to move the actuator 108 with respect to the housing 106, minus a resultant force, in the direction of arrow A, that the external thread of the nut 150 exerts on the thread of the actuator body 140 (e.g. as a result of the force from the spring 110 acting on the plunger 104 to drive rotation of the nut 150).

It can be seen that. by appropriate design of the various thread pitches and the friction element 146, the plunger apparatus can be configured to ensure that the spring force is insufficient to cause back-drive induced rotation of the nut 150 without operation of the actuator 108.

In this example, the threaded portions of the plunger apparatus 100 described above are also configured to provide an essentially one to one relationship between the actuator displacement and the plunger displacement.

In this example, there are a number of design choices that can be used to optimise the plunger apparatus 100, in particular to minimise the axial force from the nut 150 without the force effectively changing direction. These choices include, for example, selection of: the types of material used; surface finishes; thread pitches and profiles; and design of thrust bearing between nut 150 and the housing 106.

Figure 4:
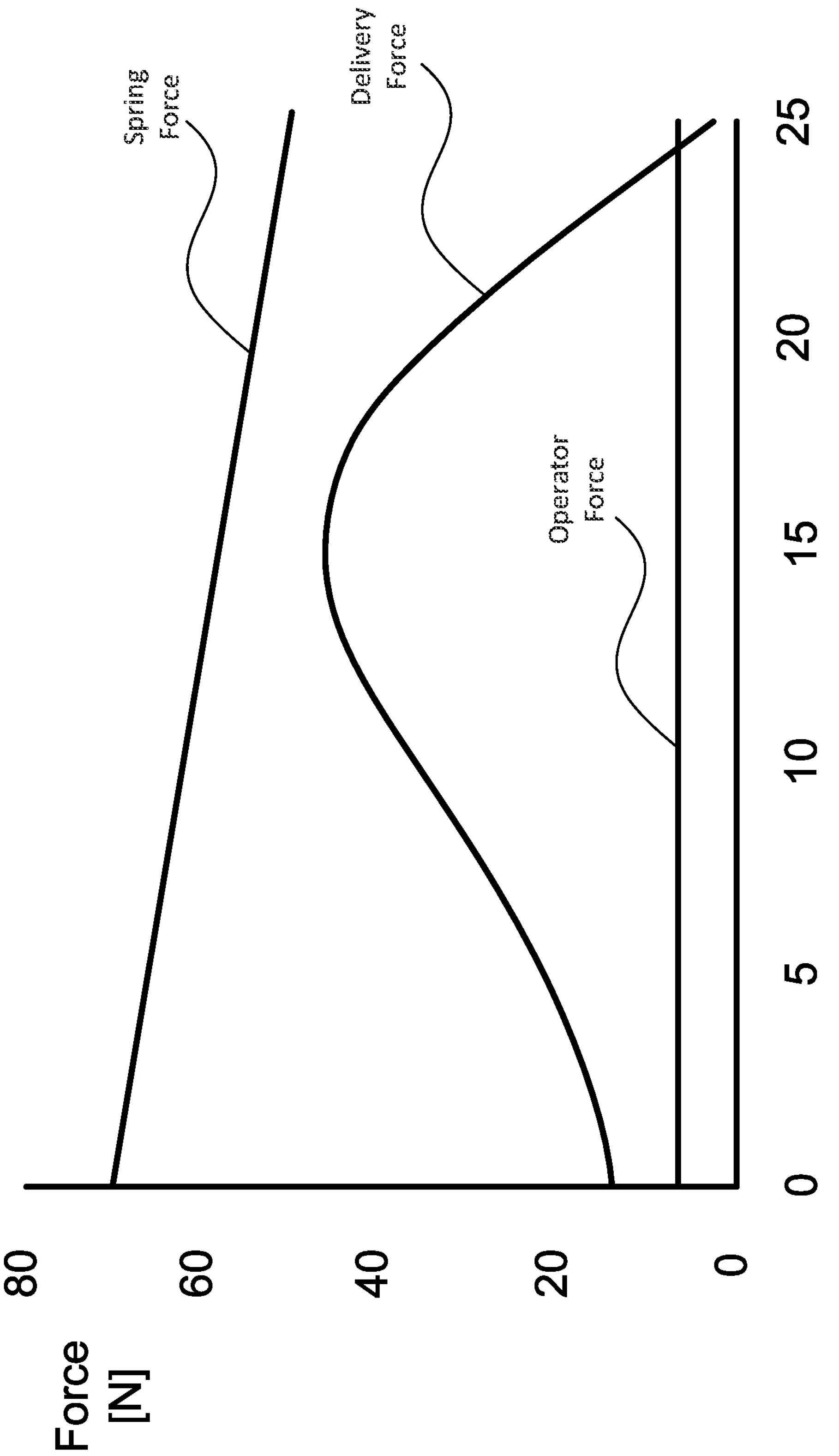
FIG. 4 is an illustration showing, conceptually, the forces acting on various parts of the exemplary plunger apparatus of FIG. 1(*a*) during operation.

FIG. 4 is an illustration showing, conceptually, the forces acting on various parts of the exemplary plunger apparatus 100 of FIG. 1(*a*) when implemented as part of an IOL delivery device, during operation, as a function of the displacement of the plunger tip 118.

As illustrated in FIG. 4, the spring force declines, substantially linearly, from its maximum value, when the spring 110 is in its pre-compressed state and the plunger tip 118 is at zero displacement, to a lower value when the IOL 102 is dispensed. The delivery force, required to deliver the IOL 102 into the eye, increases as the IOL 102 is pressed into the narrowing nozzle 114 before dropping sharply as the IOL 102 passes through the end of the nozzle 114. The operator force, required to drive the actuator 108, remains low and constant throughout the procedure.

As those skilled in the art would recognise, kinetic dry friction can be significantly less than static dry friction. Too great a difference between these frictions could result in noticeable and unwanted stiction. Accordingly, the materials used are selected to take this into account, such that stopping and starting does not result in significant peaks of the operator force.

It can be seen, therefore, that the plunger force is decoupled from the actuation force, and displacement of the actuator 106, by the operator, results in a corresponding displacement of the plunger tip 118 that can be controlled with greater precision. Thus, the plunger apparatus 100 can be used in a one-handed manner that reduces the force that an operator would otherwise have to apply, and also provides greater control.

Assembly and Storage of the Plunger Apparatus

Possible assembly and storage of the plunger apparatus will be described, by way of example only, with reference to FIG. 5 which is an illustration showing, schematically, a three-dimensional, partially exploded, sectional view of the exemplary plunger apparatus 100 of FIG. 1(*a*) during assembly. It will be appreciated that the described assembly method is illustrative and that different assembly methods may be used depending on how the plunger apparatus 100 is implemented.

Figure 5:
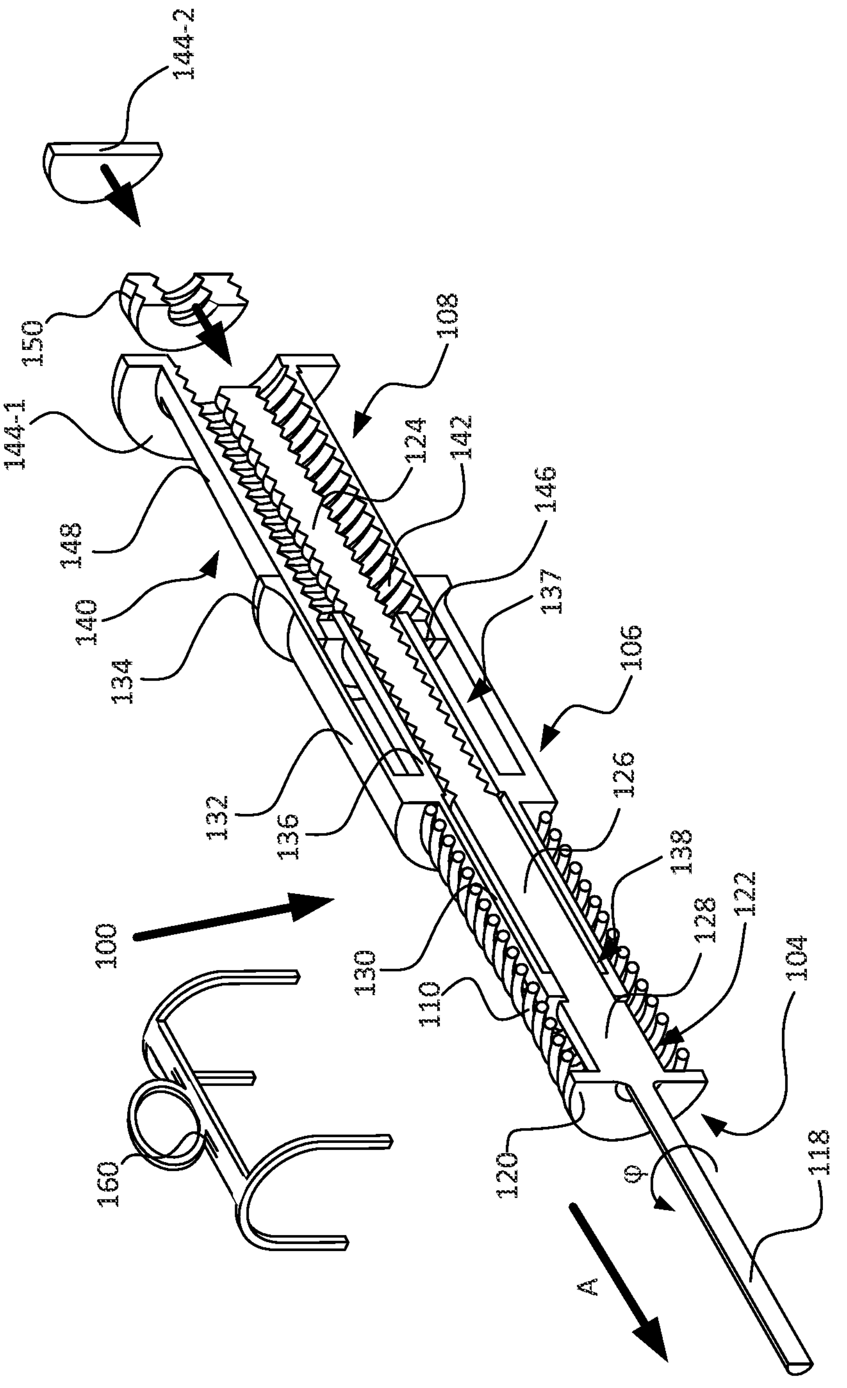
FIG. 5 is an illustration showing, schematically, a three-dimensional, partially exploded, sectional view of the exemplary plunger apparatus of FIG. 1(*a*) during assembly.

During assembly, the plunger 104, the spring 110, the housing 106, the friction element 146 and the actuator 108 are assembled together as illustrated in FIG. 5, in an initial group of assembly steps. Specifically, the spring 110 is placed over the plunger body 122 against the spring retainer 120, and the plunger 104 is inserted into the first casing portion 130 of the housing 106 and pushed to a starting position thereby compressing the spring 110. The friction element 146 is positioned at the correct location either inside the actuator body 140, or around the protruding end of the internal portion 136 of the housing 106. The actuator body 140 of the 108 is inserted into the first casing portion 130 of the housing 106 to locate the actuator 108 in its start position with the friction element 146 engaged at the correct location both inside the actuator body 140 and around the internal portion 136 of the housing 106.

To facilitate assembly and disassembly, as seen in FIG. 5, the plunger apparatus 100 of this example is configured to provide access for installation and removal of the nut 150, through the opening at the end of the actuator body 140 furthest from the plunger tip 118, by removal of the cap 144-2.

The nut 150 is offered up through the access opening in the actuator body 140 and screwed in until the nut engages against the protruding end of the internal portion 136 of the housing 106. A tool such as a tube spanner, or the like, with a pair of handling protrusions, may be provided for this purpose. Once the nut 150 reaches its end position, the plunger apparatus 100 is mechanically ready and the opening in the actuator body 140 may be covered by means of the cap 144-2.

A removable spring clip 160, or the like, may be provided for fitting over the ends of the pre-compressed spring and for bearing the load of the spring 110 during storage. The clip 160 protects the plunger apparatus 100 from creep that might otherwise arise as a result of the forces exerted by the loaded spring. The clip 160 may be removed as part of a procedure to prime the device before use.

Modifications and Alternatives

A detailed example has been described above. As those skilled in the art will appreciate a number of modifications and alternatives can be made to the above embodiments whilst still benefiting from the inventions embodied therein.

For example, it will be appreciated that, whilst the above example is described in the context of an IOL delivery device, the technical principles described may be extended to procedures outside the IOL delivery space. For example, the principles could be applied in any situation in which a medical practitioner or other operator is required to deploy a potentially high force whilst simultaneously maintaining a high level of precision and control to administer a material or object. Even where the force or precision required is not particularly great, as those skilled in the art would recognise, the features described above have the potential to reduce the risk of repetitive strain injury in any similar procedure where an operator is required routinely to administer a substance or object. In orthopaedics for instance, similar procedures may include the injection of biomaterials, bone cement and hyaluronic acid. Similar applications may be found in spinal surgery and dentistry.

It can be seen that the exemplary plunger apparatus described above is configured to avoid any backlash in the chain of components from the actuator to the plunger tip and that there is essentially a one to one relationship between the actuator position and the plunger position. This means that the concept lends itself to any application in which the accurate positioning of something at the plunger tip by controlling the displacement of the actuator. Other applications that may benefit from such control may be found in cardiology, e.g. for the placement of heart valves and stents, and neurology.

The presence of the preloaded spring, allowing the delivery device to be essentially free of backlash, means that there is the potential to use the same principles to provide a highly accurate instrument which could be used for the accurate and measurable delivery of precious drugs It will, nevertheless, be appreciated that the relation between actuator displacement and plunger displacement need not be one to one. With appropriate design, the actuator and plunger body could be configured so that a small actuator displacement leads to a large plunger displacement, which may be beneficial where the device in which the plunger apparatus is implemented is used to deliver a certain quantity of substance fast. Conversely the actuator and plunger body could be configured such that a large actuator displacement leads to a small plunger displacement (e.g. to provide more precise control at the plunger tip). The ratio between actuator and plunger displacement can essentially be configured to be a fixed number, for example whereby a 10 mm actuator displacement results in a plunger travel of, for example, 0.5 mm.

It will be appreciated that the device can be implemented either as a disposable device or as a reusable device.

It will be appreciated that whilst the use of the pre-compressed spring for providing the source of the power for driving the plunger is particularly beneficial, another source of mechanical power could be used either as an alternative to the spring or in addition to it. For example, a pneumatic actuator, or the like could be used. Such a pneumatic actuator may, for example, be powered by a source of compressed air, separate from the injector device, and ducted to the device by means of a flexible tube or the like. Compressed air is generally a readily available source of power, albeit that pneumatic actuators can sometimes be hard to control.

It will be appreciated that the spring may be arranged to be in a tensioned state for providing the source of the power for driving the plunger.

Whilst, in the example above, the rotation of the back-driven nut is controlled by the movement of the axially controlled actuator, the rotation could be controlled in other ways. For example, rotation control could be provided by a rotary damper, such as an electro-mechanical damper. The operator in this scenario may, for example, be provided with a means to switch the damper on or off and/or a wheel attached to a variable resistor to control the speed of delivery.

It will be appreciated that, whilst the threads of the example described above are chosen such that the nut is back-drivable with respect to the threaded portion of the plunger body, a plunger apparatus could be implemented in which the threads are configured such that the nut is not back-driveable with respect to the plunger. The rotation of the nut in an arrangement where it cannot be back-driven by the plunger can still be driven by an actuator as described for the above example albeit that the forces at play between nut and actuator are different as different faces of the thread profile will be engaged. For example, if the nut is not back-driveable with respect to the plunger, then the force the operator exerts on the actuator will typically be the sum of the force required to move the actuator with respect of the housing and the force the actuator exerts on the thread of the nut in order to make the nut rotate.

A mechanism may be provided in the plunger apparatus for applying a force for actively rotating the nut and hence allow the plunger to be driven forward. Whilst such a mechanism is particularly beneficial where the nut is not back-driveable it may also be used beneficially where the nut is back-driveable. For example, the rotation of the nut could be driven by electro-mechanical means, such as a geared motor or a stepper motor, where the surgeon is provided with a means to stop and start the rotation, and possibly to control the speed of delivery. An advantage of having a pre-compressed spring providing the main mechanical driving force in this case is that the motor only needs to provide a relatively low torque—i.e enough to overcome the fiction.

Alternatively, or additionally, a torsion spring may be provided in the annular cavity which is preloaded when the device is assembled. This torsion spring may be configured to act on the nut to provide an active force for rotating the nut in a direction that will operate the plunger.

In the example described with reference to the figures, neither plunger nor actuator are enabled to rotate with respect to the housing by means of keying features in the form of splines and associated groves. It will be appreciated that there are other ways to provide a similar effect. The keying features between the housing and the plunger may, for example be spiraled providing that their pitch and direction is dissimilar from the thread engagement between the plunger and the nut. In an implementation in which the interface between the plunger and the housing is threaded, the interface between the nut and the plunger could be chosen to be a straight spline.

Similarly, the interfaces between the nut and the actuator and between the actuator and the housing may be modified. The interface between the nut and the actuator could be a straight spline whereas the interface between the housing and the actuator may be threaded, or both interfaces may be threaded.

The thread between nut and actuator could be handed in the opposite direction with respect of the thread on the plunger. In this arrangement, the plunger and the actuator would travel in opposite directions, during operation, and the operator would have to pull the actuator out of the housing to allow the plunger to be driven forward.

Various other modifications will be apparent to those skilled in the art and will not be described in further detail here.

The invention claimed is:

1. Plunger apparatus for a delivery device, the plunger apparatus comprising:

- a housing;
- a plunger configured for movement in an axial direction relative to the housing for expelling at least one object and/or material from a nozzle of the delivery device, the nozzle located at a distal end of the delivery device;
- a source of stored mechanical energy configured to bias the plunger in the axial direction toward the distal end of the delivery device;
- a rotatable element held by the housing and configured for rotation relative to the housing, about an axis of rotation that is parallel to the axial direction, whereby rotation of the rotatable element through a given cumulative rotational displacement provides a controlled release of the plunger for the movement of the plunger, in the axial direction toward the distal end of the delivery device, under a force provided by the source of stored mechanical energy, for a longitudinal displacement that is dependent on the cumulative rotational displacement; and an actuator for operation by an operator of the plunger apparatus to induce rotation of the rotatable element relative to the housing to provide the controlled release of the plunger for the movement in the axial direction of the plunger under the force provided by the source of stored mechanical energy.

2. Plunger apparatus according to claim 1 wherein the plunger and the housing are mutually configured for axial movement relative to one another in which rotation of the plunger, relative to the housing as the plunger moves in the axial direction, is inhibited.

3. Plunger apparatus according to claim 1 wherein the plunger and the rotatable element each have a respective threaded surface, wherein the threaded surfaces of the plunger and the rotatable element are configured for mutual engagement whereby the rotatable element is configured for rotation relative to the plunger as the rotatable element rotates relative to the housing to provide the controlled release of the plunger.

4. Plunger apparatus according to claim 3 wherein the threaded surfaces of the plunger and the rotatable element are configured such that the rotatable element is back-drivable with respect to the plunger.

5. Plunger apparatus according to claim 3 wherein the threaded surfaces of the plunger and the rotatable element are configured for inhibiting the movement in the axial direction of the plunger, relative to the housing, when the rotatable element is not being rotated.

6. Plunger apparatus according to claim 1 wherein the rotatable element and plunger are mutually configured for axial movement relative to one another in which rotation of the rotatable element, relative to the plunger, as the plunger moves in the axial direction, is inhibited.

7. Plunger apparatus according to claim 1 wherein the plunger and the housing each have a respective threaded surface, wherein the threaded surfaces of the plunger and the housing are configured for mutual engagement whereby the plunger is configured for rotation relative to the housing, as the rotatable element rotates relative to the housing, to provide the controlled release of the plunger.

8. Plunger apparatus according to claim 1 wherein the rotatable element and housing are mutually configured for rotational movement relative to one another in which axial movement of the rotatable element, relative to the housing, is inhibited.

9. Plunger apparatus according to claim 1 wherein the source of stored mechanical energy comprises a spring that is arranged for storing elastic potential energy prior to actuation of the plunger apparatus for providing the force for driving the movement of the plunger.

10. Plunger apparatus according to claim 9 wherein the spring is arranged to be in a compressed state for storing the elastic potential energy prior to actuation of the plunger apparatus for providing the force for driving the movement of the plunger.

11. Plunger apparatus according to claim 1 wherein the source of stored mechanical energy comprises a pneumatic actuator for providing a pneumatic force as the force for driving the movement of the plunger.

12. Plunger apparatus according to claim 1 wherein the actuator is configured for axial movement, by the operator, relative to the housing whereby the axial movement of the actuator induces the rotation of the rotatable element relative to the housing to provide the controlled release of the plunger.

13. Plunger apparatus according to claim 1 wherein the actuator and the housing are mutually configured for axial movement relative to one another in which rotation of the actuator, relative to the housing as the actuator is moved in the axial direction, is inhibited.

14. Plunger apparatus according to claim 1 wherein the actuator and the rotatable element each have a respective threaded surface, wherein the threaded surfaces of the actuator and the rotatable element are configured for mutual engagement whereby the rotatable element is configured for rotation relative to the actuator, as the actuator is moved in the axial direction, whereby to provide the controlled release of the plunger.

15. Plunger apparatus according to claim 14 wherein the threaded surfaces of the actuator and the rotatable element are configured such that the rotatable element is back-drivable with respect to the actuator.

16. Plunger apparatus according to claim 1 wherein the rotatable element and actuator are mutually configured for axial movement relative to one another in which rotation of the rotatable element, relative to the actuator, as the actuator moves in the axial direction, is inhibited.

17. Plunger apparatus according to claim 1 wherein the actuator and the housing each have a respective threaded surface, wherein the threaded surfaces of the actuator and the housing are configured for mutual engagement whereby the actuator is configured for rotation relative to the housing, to rotate the rotatable element relative to the housing whereby to provide the controlled release of the plunger.

18. Plunger apparatus according to claim 1 wherein the actuator is provided with an electro-mechanical mechanism for driving rotation of the rotatable element relative to the housing and a switch for operation of the electro-mechanical mechanism, by an operator, to control operation of the rotatable element whereby to provide the controlled release of the plunger.

19. Plunger apparatus according to claim 1 further comprising at least one further source of mechanical energy for providing a force for driving the rotation of the rotatable element.

20. Plunger apparatus according to claim 1 further comprising at least one element for providing a preconfigured resistance between the actuator and the housing for resisting axial movement of the actuator relative to the housing whereby the actuator is moveable by an operator applying a substantially uniform force that is sufficient for overcoming the preconfigured resistance.

21. Plunger apparatus according to claim 1 wherein the housing, plunger, rotatable element and the actuator are mutually configured for operation of the actuator by an operator applying a substantially uniform force for moving the actuator in the axial direction, whereby to rotate the rotatable element relative to the housing to provide the controlled release of the plunger; from a first position relative to the housing in which the plunger apparatus is primed for use; to a second position relative to the housing in which the plunger apparatus is configured to expel the at least one object and/or material from the nozzle of the delivery device in operation.

22. A delivery device for expelling at least one object and/or material, the delivery device comprising a nozzle for expelling the at least one object and/or material and a plunger apparatus as claimed in claim 1.

23. A delivery device according to claim 22 wherein the delivery device is configured for expelling an intraocular lens into an eye of a patient.

24. A method of manufacturing a plunger apparatus according to claim 1, the method comprising:

providing the housing, the plunger, the source of stored mechanical energy, the rotatable element, and the actuator of the plunger apparatus according to claim 1; and assembling the housing, the plunger, the source of stored mechanical energy, the rotatable element, and the actuator to form the plunger apparatus according to claim 1.

* * * * *